United States Patent
Lotte (12)

(10) Patent No.: US 6,364,659 B1
(45) Date of Patent: Apr. 2, 2002

(54) ORTHODONTIC BITE OPENER

(75) Inventor: Brian W. Lotte, Hermosa Beach, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/511,522

(22) Filed: Feb. 23, 2000

(51) Int. Cl.$^7$ .................................................. A61C 3/00
(52) U.S. Cl. ................................ 433/8; 433/18; 433/24
(58) Field of Search ....................................... 433/8–24

(56) References Cited

U.S. PATENT DOCUMENTS

| | | |
|---|---|---|
| 3,337,957 A | 8/1967 | Reed |
| 3,395,455 A | 8/1968 | Overby et al. |
| 3,462,838 A | 8/1969 | Alstergren |
| 3,675,327 A | 7/1972 | Huget et al. |
| 4,470,809 A | 9/1984 | Klepacki |
| 4,504,229 A | 3/1985 | Garito et al. |
| 4,516,938 A | 5/1985 | Hall |
| 4,533,320 A | 8/1985 | Piekarsky |
| 4,557,692 A | 12/1985 | Chobajian |
| 4,609,350 A | 9/1986 | Krause |
| 4,614,497 A | 9/1986 | Kurz |
| 4,915,630 A | 4/1990 | Honig |
| 4,950,158 A | 8/1990 | Barngrover et al. |
| 5,366,372 A | 11/1994 | Hansen et al. |
| 5,439,379 A | 8/1995 | Hansen |
| 5,848,891 A | 12/1998 | Eckhart et al. |
| 5,879,156 A | 3/1999 | DeLeo |
| 5,885,073 A | 3/1999 | Kussick |
| 5,957,686 A | 9/1999 | Anthony |
| 6,017,216 A | 1/2000 | DeLeo |

OTHER PUBLICATIONS

Lingual Brackets; Refined Lingual Appliance System from Ormco, 1987, 1 page.
Ormco Bite Turbos, 1 page, Ormco web site, copyright 1999.
"Lingual Orthodontics: A Status Report; Part 2 Research and Development" Journal of Clinical Orthodontics, Nov. 1982.
"Dr. Vincent M. Kelly, on Lingual Orthodontics"; Journal of Clinical Orthodontics; vol. 16, No. 7, Jul. , 1982.
"Lingual Orthodontics; A Status Report" Journal of Clinical Orthodontics, Apr. 1982.
"Keys to Success in Lingual Therapy, Part I"; Journal of Clinical Orthodontics, Apr., 1986.
"Lingual Orthodontics: A Status Report: Part 5"; Journal of Clinical Orthodontics, Feb., 1983.
"Torque/Angulation Reference Guide", copyright 1984, brochure.
"Indirect–Bonded Bite Plate to Prevent Impingement on Ceramic Brackets"; Journal of Clinical Orthodontics, vol. 26, No. 4, 1992.
"Treatment of Deep Bite with Bonded Biteplanes"; Journal of Clinical Orthodontics, Jul., 1996.
"Lingual Orthodontics: A Status Report: Part 4, Diagnosis and Treatment Planning"; Journal of Clinical Orthodontics, Jan., 1983.

*Primary Examiner*—Nicholas D. Lucchesi
(74) *Attorney, Agent, or Firm*—James D. Christoff

(57) ABSTRACT

A bite opener for use during orthodontic treatment has a base for mounting on a lingual side of a tooth, as well as at least one occlusal portion for contact with an opposing tooth so that other teeth (such as molar teeth) can be extruded. In one embodiment, the bite opener has a channel extending between a mesial section and a distal section, so that the sections can be squeezed together when desired to debond the bite opener from the patient's tooth. In other embodiments, the bite opener includes a bite plate connected to the body, and the bite plate is made of a material softer than the body to enhance patient comfort when the jaws are closed. Optionally, the bite plate is detachably connected to the body so that the bite plate can be removed before debonding the body from the tooth.

25 Claims, 2 Drawing Sheets

ORTHODONTIC BITE OPENER

BACKGROUND OF THE INVENTION

1. Field of the Invention

This invention relates to an appliance used in orthodontic treatment. More particularly, the present invention relates to a bite opener for reducing overbite or excessive overlap of one jaw relative to the other.

2. Description of the Related Art

Orthodontic treatment involves movement of malpositioned teeth to orthodontically correct locations. Orthodontic treatment can greatly improve the patient's occlusion so that the teeth's function is enhanced during biting and chewing. Moreover, straightening of crooked teeth can dramatically enhance the patient's appearance.

One type of problem that is sometimes faced during orthodontic treatment is the correction of deep overbites that occur in anterior regions (i.e., front regions) of the oral cavity. Deep overbites exist when the upper or maxillary front teeth overlap the lower or mandibular front teeth by an undue amount. It is normally desired to correct deep overbites when possible in order to improve the overall appearance of the patient's dentition.

Deep anterior overbites can be corrected during orthodontic treatment by extruding the posterior teeth (i.e., teeth located in rear portions of the oral cavity on both sides of the dental arch, including the molar teeth and bicuspid teeth). However, a significant amount of force is normally placed on the patient's posterior teeth during normal opening and closing movements of the patient's jaws. For this reason, it is generally not feasible to attempt to shift the posterior teeth as a group by using springs or force-inducing wires, since the force exerted on the posterior teeth by the patient's jaws is normally much larger than the force that could be applied by such springs or wires.

One technique for correcting deep anterior overbites involves the use of tiny appliances that are bonded to the lingual side of the patient's upper teeth (i.e., the side of the patient's upper teeth that face inwardly toward the patient's tongue). These appliances, sometimes referred to as bite openers, have a contact surface that extends in a direction that is generally parallel to the occlusal plane (i.e., a reference plane that is generally horizontal when the patient is upright and extends between the biting surfaces of the upper jaw and the lower jaw). Often, the bite openers are bonded to the patient's two upper central incisor teeth so that two contact surfaces are presented to the opposing, lower central incisor teeth when the patient's jaws are closed.

The contact surfaces of bite openers function to prevent the jaws from fully closing such that the patient's lower posterior teeth do not contact the upper posterior teeth when the lower incisor teeth engage the bite opener. The resulting space between the upper posterior teeth and the lower posterior teeth enables each posterior tooth to be extruded over time in directions toward the opposing tooth. In many instances, the posterior teeth will extrude sufficiently to contact each other again and reestablish occlusion after only six or eight weeks of use of the bite opener.

Examples of appliances for opening the bite and correcting deep overbites are described in U.S. Pat. Nos. 4,915,630 and 5,957,686. These types of appliances are favored by many practitioners because they are bonded to the teeth during treatment and issues of patient compliance are avoided. Removable appliances are also possible, but can significantly increase the overall length of treatment time if the patient does not cooperate and wear the appliance as instructed.

However, there is a continuing need in the art to improve existing appliances used in orthodontic treatment so that the practitioner's efficiency can be enhanced wherever possible. It is also desirable to improve the functional characteristics of existing appliances, so that the appliances provide optimal results during the course of treatment.

SUMMARY OF THE INVENTION

The present invention is directed toward an improved orthodontic bite opener having features that enhance patient comfort during use and facilitate removal of the bite opener from the oral cavity at the conclusion of its use. In one embodiment of the invention, the bite opener has a channel between mesial and distal sections, so that the bite opener can be easily debonded from the lingual surface of the tooth by squeezing the mesial and distal sections together. In another embodiment, the bite opener has a soft bite plate that is positioned for contact with the occlusal tips of the opposing teeth when the patient's jaws are closed. Optionally, the bite plate is detachable from a body of the opener.

In more detail, the present invention in one aspect is directed toward an orthodontic bite opener that comprises a base for mounting the bite opener on a lingual side of the tooth. The bite opener also includes a mesial section connected to the base and a distal section connected to the base. Each of the mesial section and the distal section has an occlusal surface portion that extends in a reference plane generally parallel to the occlusal plane when the base is mounted on a lingual side of the tooth. The mesial section is spaced from the distal section to present a channel therebetween. The channel extends in a generally occlusal-gingival direction and provides a space for movement of at least one section toward the other section in order to facilitate debonding the bite opener from the tooth.

Another aspect of the present invention is directed toward an orthodontic bite opener that comprises a base for mounting the bite opener on a lingual side of the tooth and a body connected to the base. The body has at least one occlusal surface portion that extends in a reference plane generally parallel to the occlusal plane when the base is mounted on a lingual side of the tooth. The body also has a mesial outer edge and a distal outer edge that converge toward each other as the base is approached in directions along the occlusal surface portion.

The present invention is also directed toward an orthodontic bite opener that comprises a base for mounting the bite opener on a lingual side of the tooth and a body connected to the base. The body has a mesial section, a distal section and a channel extending, in a generally occlusal-gingival direction between the mesial section and the distal section. The bite opener also includes a bite plate connected to the body. The bite plate has at least one occlusal surface portion that extends in a reference plane generally parallel to the occlusal plane when the base is mounted on a lingual side of the tooth. The bite plate is made of a material having a hardness that is less than the hardness of the body.

Another aspect of the present invention is directed toward an orthodontic bite opener that comprises a base for mounting the bite opener on a lingual side of the tooth, a body connected to the base and a bite plate. The bite plate includes at least one occlusal surface portion that extends in a reference plane generally parallel to the occlusal plane. The bite plate is detachably connected to the body.

These and other aspects of the invention are described in more detail below and are illustrated in the accompanying drawings.

BRIEF DESCRIPTION OF THE INVENTION

DETAILED DESCRIPTION OF THE PREFERRED EMBODIMENTS

Although the disclosure set out below is detailed in order to enable those skilled in the art to practice the invention, the embodiments disclosed herein are to be considered only examples of the invention which may be embodied in other specific structures as well.

An orthodontic bite opener according to one embodiment of the invention is illustrated in FIGS. 1–4 and is broadly designated by the numeral 10. The bite opener 10 includes a base 12 for mounting the bite opener 10 on a lingual side of the tooth. Preferably, the base 12 is directly mounted to the tooth surface by the use of an adhesive, such as a light curable adhesive or a two component adhesive that cures after the components are mixed together. An example of a suitable adhesive is "Transbond XT" brand adhesive from 3M Unitek Corporation.

Figure 4:
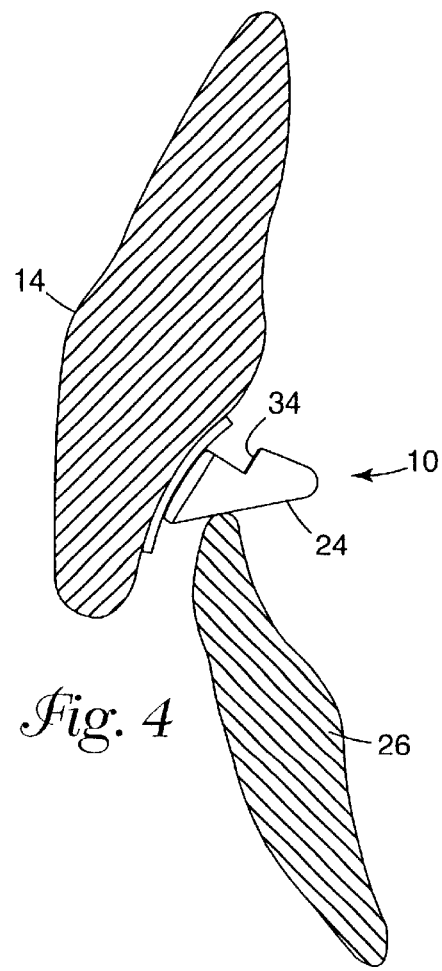
FIG. 4 is a side cross-sectional view taken through a representative upper front tooth and lower front tooth of a patient undergoing orthodontic treatment, wherein the bite opener shown in FIGS. 1–3 is mounted on a lingual surface of the upper tooth.

Preferably, the outer, tooth-facing surface of the base 12 has a compound convex configuration that is curved in at least one direction. Preferably, the base 12 is curved in an arc as the occlusal edge (i.e., the outer tip) of the tooth is approached. As shown in FIG. 4, the convex configuration of the base 12 matches the concave configuration of the region of a patient's upper tooth 14 where the bite opener 10 is typically mounted.

Preferably, the base 12 includes structure for enhancing the bond of the bite opener 10 to the tooth 14. An example of a suitable structure is a mesh pad that resembles a fine wire mesh screen with small openings. Preferably, the wire mesh is brazed to a thin metal foil along its lingual side. Optionally, the mesh is roughened, etched or otherwise surface treated in order to further enhance the strength of the bond between the bite opener 10 and the tooth 14.

As another example, the base 12 could be an integral, one-piece construction. In this embodiment, the base 12 preferably has dovetail-shaped grooves, a series of upstanding pegs with enlarged heads or other structure that provides overhanging regions. Once the adhesive bonding the bite opener 10 to the tooth 14 has hardened, the overhanging regions provide a mechanical interlock between the adhesive and the base 12.

The bite opener 10 also includes a body 16 that is connected to the base 12. If the base 12 includes a mesh pad, the base 12 may be brazed or welded to the body 16. Alternatively, if the base 12 is made of integral construction, it is preferred that the bite opener 10 also be made as part of the same one-piece construction such that the body 16 is integrally connected to the base 12.

Figure 3:
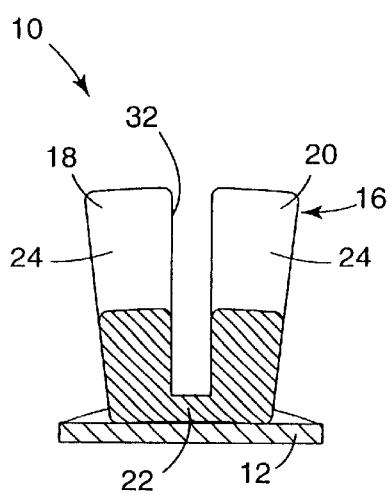
FIG. 3 is another side cross-sectional view of the bite opener depicted in FIG. 1, taken along lines 3—3 of FIG. 1.

The body 16 includes a mesial section 18 and a distal section 20. The body 16 also has a labial section 22 that integrally interconnects the mesial section 18 and the distal section 20. As shown in FIG. 3, the sections 18, 20, 22 present an overall, generally "U"-shaped configuration when viewing the bite opener in a gingival direction (i.e., in a direction toward the patient's gingiva or gums) or in an occlusal direction (i.e., in a direction toward the occlusal edge or outer tips of the patient's tooth).

The mesial section 18 and the distal section 20 each have an occlusal surface portion 24 that faces the occlusal edge of the opposing tooth, such as the lower front anterior tooth 26 illustrated in FIG. 4. Preferably, the surface portions 24 extend in a generally flat reference plane that is generally parallel to the occlusal plane of the patient when the base 12 is mounted on the upper tooth 14. If desired as an alternative, however, the surface portions 24 may instead extend in a slightly curved reference plane that is also (within the bounds of the surface portions 24) generally parallel to the patient's occlusal plane. If the surface portions 24 are curved, they preferably present a concave configuration that could optionally be used to guide the occlusal tips of the opposing teeth toward a certain position that lies at the deepest part of the concavity when the patient's jaws are closed.

The surface portion 24 of the mesial section 18 presents a mesial outer edge 28. The surface portion 24 of the distal section 20 presents a distal outer edge 30. Preferably, the outer edges 28, 30 converge toward each other as the base 12 is approached in directions along the occlusal surface portions 24. An example of a suitable angle of convergence is 20 degrees (i.e., each of the edges 28, 30 is oriented 10 degrees from a central reference axis extending between the sections 18, 20), although other angles of convergence are also possible. The convergence is useful for presenting a wider area for the surface portions 24 for contact with opposing teeth, while still maintaining a relatively small "footprint" of area near the base 12.

The body 16 also has a channel 32 that is located between the mesial section 18 and the distal section 20. As shown, for example, in FIG. 3, the channel 32 extends from the labial section 22 to the outer lingual end of the sections 18, 20. The channel 32 lies along an occlusal-gingival reference axis when the bite opener is mounted on the tooth 14, although other constructions are also possible.

The channel 32 advantageously provides a space for movement of the sections 18, 20 in directions toward each other when it is desired to debond the bite opener 10 from the tooth 14. To debond the bite opener 10, a pair of orthodontic pliers is moved to engage a mesial side of the mesial section 18 and a distal side of the distal section 20. Next, the pliers are manipulated to close the jaws of the pliers and squeeze the sections 18, 20 in directions toward each other. As the jaws of the pliers are closed and the sections 18, 20 pivoted toward each other, a crack is initiated in the adhesive and the base 12 is readily detached from the lingual surface of the tooth 14.

Advantageously, the channel 32 provides a space for movement of the sections 18, 20 toward each other to collapse the bite opener 10. During debonding, the base 12 and the labial section 22 bend to a concave configuration as the sections 18, 20 are squeezed together. The total amount of bending need not be relatively large, since orthodontic adhesives are typically brittle and the base 12 can be normally detached from the tooth 14 with ease once a crack has started to propagate through the adhesive.

The mesial section 18 and the distal section 20 also each include a notch 34 that faces the base 12 and is located along a gingival side of the bite opener 10. The notches 34 facilitate gripping the bite opener 10 and manipulation of the bite opener 10 when desired. For example, the notches 34 can be gripped by serrations provided on jaws of a pair of pliers used by the practitioner during placement of the bite opener 10, so that the base 12 can be pushed toward the tooth 14 and firmly seated in the adhesive.

The body 16 may be made of any material suitable for use in the oral cavity that has sufficient strength to function as intended during the course of treatment and satisfactorily withstand expected biting forces from the opposing tooth. An example of a suitable material is a metallic material, such as series 300 stainless steel. If desired, the body 16 (including the surface portions 24) may be coated with a softer material, such as a synthetic resinous material. As another alternative, the body 16 may be entirely made of a synthetic resin material such as acrylic or fiber reinforced polycarbonate.

Figure 1:
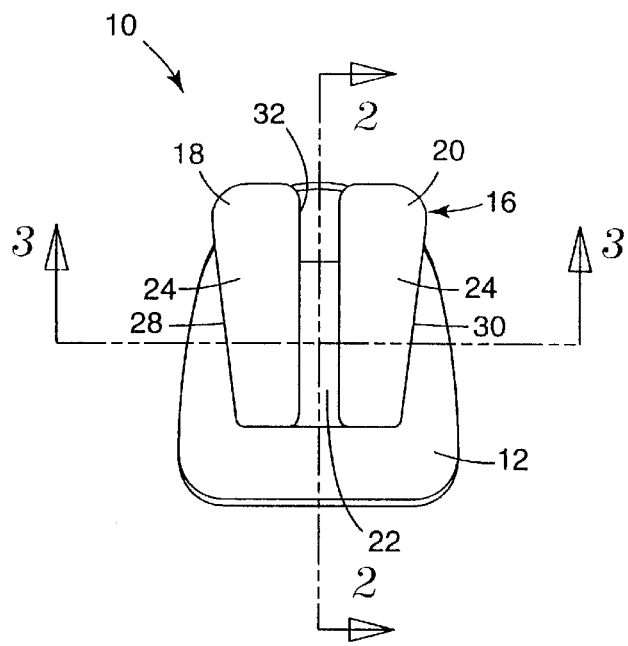
FIG. 1 is a front elevational view of an orthodontic bite opener constructed in accordance with one embodiment of the invention, and looking in a direction toward a base of the bite opener.
Figure 2:
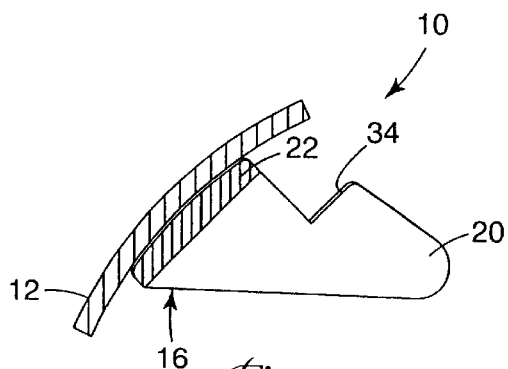
FIG. 2 is a side cross-sectional view of the bite opener illustrated in FIG. 1 and taken along lines 2—2 of FIG. 1.

Preferably, the various corners and edges of the bite opener 10 are suitably rounded in order to reduce irritation to the patient's tongue. For example, and as shown in FIGS. 1 and 2, the outer tip of the mesial section 18 and the distal section 20 has a smoothly curved outer corner at its widest region. Other corners and edges of the body 16 are rounded as well.

Figure 5:
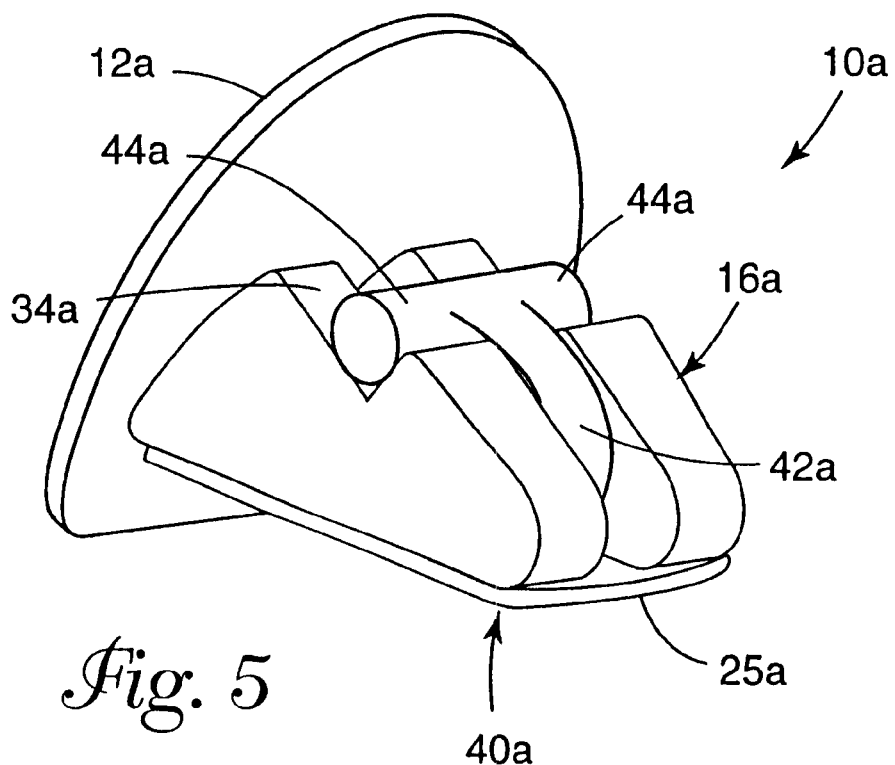
FIG. 5 is a perspective view of an orthodontic bite opener that is constructed according to another embodiment of the invention, wherein the bite opener includes a detachable bite plate.
Figure 6:
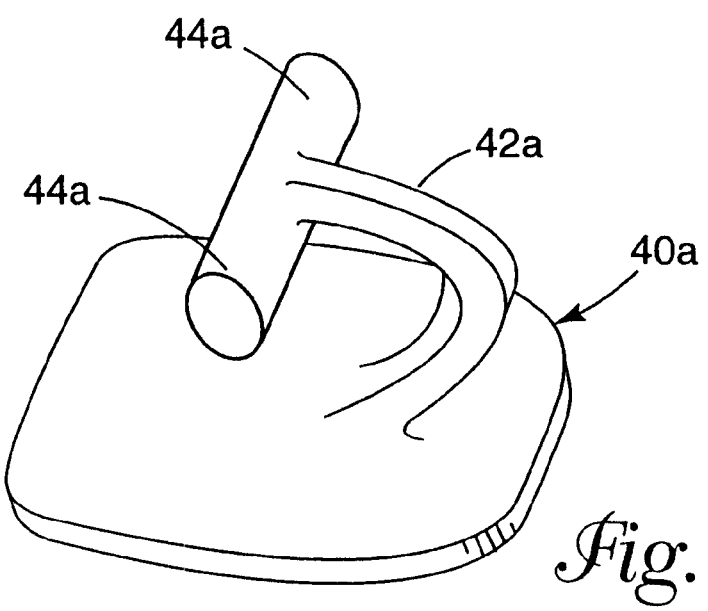
FIG. 6 is a perspective view of the bite plate alone that is shown in FIG. 5, showing the bite plate from a somewhat different angle of view.

A bite opener 10a constructed in accordance with another embodiment of the invention is illustrated in FIGS. 5–6. The bite opener 10a includes a base 12a as well as a body 16a. In this embodiment, the base 12a is identical to the base 12 and the body 16a is identical to the base 16, and as such a detailed description of such elements need not be repeated.

The bite opener 10a includes a bite plate 40a that is connected to the body 16a. The bite plate 40a is shown alone in FIG. 6. Preferably, the bite plate 40a is made of a material having a hardness that is less than the hardness of the body 16a. For example, if the body 16a is made of stainless steel, the bite plate 40a could be made of a synthetic resin material such as acrylic. Optionally, the bite plate 40a is made of a material that is flexible and resilient, such as a non-staining elastomer.

The bite plate 40a extends along occlusal surface portions of mesial and distal sections of the body 16a. The occlusal surface portions of the body 16a are not numbered in the drawings, but are identical to the surface portions 24 described above. The bite plate 40a also has an occlusal surface portion 25a that preferably extends in a flat or slightly curved (preferably concave) reference plane that is generally parallel to the patient's occlusal plane. The bite plate 40a as shown in FIGS. 5–7 has a generally flat configuration with a uniform thickness, although other constructions are also possible.

The occlusal surface portion 25a of the bite plate 40a provides a contact surface for contact with the occlusal edge of the opposing, lower tooth when the patient's jaws are closed. Consequently, when the bite plate 40a is made of a relatively soft, resilient material, the comfort of the patient can be enhanced. Specifically, the occlusal surface portion 25a provides a soft surface for contact with the opposing tooth so that a relatively hard surface is not encountered whenever the patient's jaws are closed.

Preferably, the bite plate 40a is detachably connected to the body 16a for removal from the body 16a when desired. For example, it may be desired to detach the bite plate 40a before debonding the bite opener 10a from the tooth. The bite plate 40a may be detachably connected to the body 16a by any one of a number of possible methods, including by the use of an adhesive that bonds the bite plate 40a to the occlusal surface portions or by the use of tabs or other structure that mechanically interlocks in detachable manner to the body 16a.

In the embodiment shown in the drawings, the bite plate 40a is detachably connected to the body 16a by means of a tab 42a that extends in a channel 32a of the body 16a. The tab 42a has an inherently curved configuration in its normal, relaxed shape as shown in FIG. 6. The tab 42a includes a pair of opposed, outwardly extending protrusions 44a that are received in respective notches 34a of the body 16a when the bite plate 40a is connected to the body 16a. Preferably, the protrusions 44a extend past the sides of the body 16a as illustrated in FIG. 5.

In use, the protrusions 44a and the tab 42a retain the bite plate 40a in secure connection to the body 16a during chewing, opening and closing of the jaws and other normal jaw movements. However, the bite plate 40a can be removed from the body 16a when desired by application of a force on the protrusions 44a in a direction away from the surface portion 25a to straighten the tab 42a. Once the tab 42a has straightened, the protrusions 44a can be lifted free from the notches 34a so that the bite plate 40a can be detached.

Other constructions are also possible. For example, the bite plate 40a could have a strap-like tab in the shape of a loop that extends along mesial and distal sides of the body 16a and connects to opposite sides of the surface portion. This tab could be readily cut when desired by use of a small knife or wire cutters. Once the tab is severed, the bite plate 40a can be easily lifted away from the body 16a. As another option, the bite plate 40a could be made of an elastomeric material that is sufficiently flexible that the loop could be stretched a sufficient distance to clear the notches 34a.

In the examples described above, the bite openers 10, 10a have been described for use on the patient's upper teeth for contact with the patient's opposing lower teeth when the jaws are closed. However, the bite openers 10, 10a may also be useful in certain instances for patients having a condition known as a "Class III" malocclusion, wherein the lower anterior teeth overlap the labial side of the opposing upper anterior teeth. In that instance, the bite openers 10, 10a are placed on lingual surfaces of the lower front teeth for contact with the occlusal tips of the upper teeth.

Additionally, more than two bite openers 10, 10a may be used at one time. For example, it may be desirable to bond the bite openers 10, 10a to the lingual surfaces of the patient's upper central incisors as well as the patient's upper lateral incisors. In that instance, the bite openers 10, 10a would contact corresponding central incisors and lateral incisors of the mandible when the patient's jaws are closed.

Those skilled in the art may recognize that other modifications and additions are possible without departing from the essence of the invention. Accordingly, the scope of the invention should not be deemed limited to the specific embodiments that are described in detail above, but instead only by a fair reading of the claims that follow along with their equivalents.

What is claimed is:

1. An orthodontic bite opener comprising:
   a base for mounting the bite opener on a lingual side of a tooth;

a mesial section connected to the base; and a distal section connected to the base, each of the mesial section and the distal section having an occlusal surface portion that extends in a reference plane generally parallel to the occlusal plane when the base is mounted on a lingual side of a tooth, and wherein the mesial section is spaced from the distal section to present a channel therebetween, the channel extending in a generally occlusal-gingival direction and providing a space for movement of at least one section toward the other section in order to facilitate debonding the bite opener from the tooth.

2. An orthodontic bite opener according to claim 1 wherein the base has an outer, generally convex configuration.

3. An orthodontic bite opener according to claim 2 wherein the base includes a layer of a mesh material.

4. An orthodontic bite opener according to claim 2 wherein the base is solid and integrally connected to the mesial section and the distal section.

5. An orthodontic bite opener according to claim 4 wherein the base includes structure for enhancing the bond of the bite opener to the tooth.

6. An orthodontic bite opener according to claim 1 wherein the mesial section and the distal section are comprised of a synthetic resin material.

7. An orthodontic bite opener according to claim 6 wherein the synthetic resin material is an acrylic material.

8. An orthodontic bite opener according to claim 6 wherein the mesial section and the distal section are also comprised of a metallic material, and wherein the synthetic resin material is a layer that extends at least partially over the metallic material.

9. An orthodontic bite opener according to claim 6 wherein the mesial section and the distal section consist essentially of the synthetic resin material.

10. An orthodontic bite opener according to claim 1 wherein the mesial section and the distal section each include a notch located adjacent the base and remote from the occlusal surface portion.

11. An orthodontic bite opener according to claim 1 wherein the mesial section and the distal section have outer edges that converge toward each other as the base is approached in directions along the occlusal surface portions.

12. An orthodontic bite opener according to claim 1 and including a bite plate detachably connected to at least one of the mesial section and the distal section.

13. An orthodontic bite opener comprising:
a base for mounting the bite opener on a lingual side of a tooth; and
a body connected to the base, the body having at least one occlusal surface portion that extends in a reference plane generally parallel to the occlusal plane when the base is mounted on a lingual side of a tooth, and wherein the body also has a mesial outer edge and a distal outer edge that converge toward each other as the base is approached in directions along the occlusal surface portion.

14. An orthodontic bite opener according to claim 13 wherein the base has an outer, generally convex configuration.

15. An orthodontic bite opener according to claim 13 wherein the mesial section and the distal section are comprised of a synthetic resin material.

16. An orthodontic bite opener according to claim 13 and including a bite plate detachably connected to at least one of the mesial section and the distal section.

17. An orthodontic bite opener comprising:
a base for mounting the bite opener on a lingual side of a tooth;
a body connected to the base, the body having a mesial section, a distal section and a channel extending in a generally occlusal-gingival direction between the mesial section and the gingival section; and
a bite plate connected to the body, wherein the bite plate has at least one occlusal surface portion that extends in a reference plane generally parallel to the occlusal plane, and wherein the bite plate is made of a material having a hardness that is less than the hardness of the body.

18. An orthodontic bite opener according to claim 17 wherein the bite plate is detachably connected to the body.

19. An orthodontic bite opener according to claim 17 wherein the base has an outer, generally convex configuration.

20. An orthodontic bite opener according to claim 17 wherein the bite plate has an occlusal portion presenting the at least one occlusal surface portion, and wherein the occlusal portion has a generally flat configuration.

21. An orthodontic bite opener according to claim 17 wherein the bite plate includes a tab that extends into the channel when the bite plate is connected to the body.

22. An orthodontic bite opener according to claim 21 wherein the tab also includes at least one protrusion for retaining the bite plate on the body.

23. An orthodontic bite opener comprising:
a base for mounting the bite opener on a lingual side of a tooth;
a body connected to the base; and
a bite plate having an occlusal surface portion that extends in a reference plane generally parallel to the occlusal plane, and wherein the bite plate is detachably connected to the body.

24. An orthodontic bite opener according to claim 23 wherein the body includes a mesial section, a distal section and a channel located between the mesial section and the distal section, and wherein the bite plate includes a tab extending into the channel.

25. An orthodontic bite opener according to claim 24 wherein the tab also includes at least one protrusion for retaining the bite plate on the body.

* * * * *